(12) United States Patent
Abele et al.

(10) Patent No.: US 8,159,743 B2
(45) Date of Patent: Apr. 17, 2012

(54) SURGICAL MICROSCOPE HAVING AN ILLUMINATING ARRANGEMENT

(75) Inventors: Alfons Abele, Schwäbisch Gmünd (DE);
Peter Reimer, Ellwangen (DE);
Andreas Negele, Oberkochen (DE);
Franz Merz, Aalen (DE); Jürgen Liegel, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 81 days.

(21) Appl. No.: 12/805,571

(22) Filed: Aug. 6, 2010

(65) Prior Publication Data

US 2011/0038040 A1    Feb. 17, 2011

Related U.S. Application Data

(60) Provisional application No. 61/272,039, filed on Aug. 11, 2009.

(30) Foreign Application Priority Data

Aug. 11, 2009 (DE) .......................... 10 2009 036 913

(51) Int. Cl.
*G02B 21/22* (2006.01)
(52) U.S. Cl. ....................................... 359/377; 359/390
(58) Field of Classification Search .......... 359/372–378, 359/385, 388–390
See application file for complete search history.

(56) References Cited

U.S. PATENT DOCUMENTS

| 5,126,877 | A | * | 6/1992 | Biber | 359/389 |
|---|---|---|---|---|---|
| 5,627,613 | A | * | 5/1997 | Kaneko | 351/221 |
| 5,760,952 | A | | 6/1998 | Koetke | |
| 6,624,932 | B2 | * | 9/2003 | Koetke | 359/389 |
| 6,975,451 | B2 | * | 12/2005 | Sander | 359/389 |
| 7,072,104 | B2 | * | 7/2006 | Okamura et al. | 359/385 |
| 7,102,818 | B2 | * | 9/2006 | Sander | 359/389 |
| 7,142,359 | B2 | * | 11/2006 | Sander | 359/385 |
| 7,307,785 | B2 | * | 12/2007 | Obrebski et al. | 359/389 |
| 7,889,423 | B2 | * | 2/2011 | Reimer et al. | 359/368 |
| 2003/0048528 | A1 | * | 3/2003 | Deverin et al. | 359/376 |
| 2006/0238711 | A1 | | 10/2006 | Kitajima | |
| 2006/0275002 | A1 | | 12/2006 | Knoblich et al. | |
| 2008/0297892 | A1 | | 12/2008 | Abele et al. | |
| 2011/0261324 | A1 | * | 10/2011 | Sander | 351/221 |
| 2011/0292180 | A1 | * | 12/2011 | Sander | 348/46 |

FOREIGN PATENT DOCUMENTS

| DE | 4214445 A1 | * | 11/1993 |
|---|---|---|---|
| EP | 1 300 109 | | 4/2003 |
| JP | 62044710 A | * | 2/1987 |

* cited by examiner

*Primary Examiner* — Mark Consilvio
(74) *Attorney, Agent, or Firm* — Walter Ottesen

(57) ABSTRACT

The invention relates to a surgical microscope having a microscope main objective for the visualization of an object plane in an object region. The objective is passed through by a first stereoscopic component beam path and by a second stereoscopic component beam path. The ophthalmologic surgical microscope includes an adjustable illuminating arrangement which makes illuminating light available. The illuminating arrangement has an illuminating optic having a beam deflecting unit which is mounted on the side of the objective facing away from the object region in order to direct the illuminating light through the objective to the object region. In a first position of the illuminating arrangement, the illuminating light passes through the cross sectional area of the objective in an area section, which at least partially surrounds the optical axis of the first stereoscopic component beam path and/or the optical axis of the second stereoscopic component beam path.

26 Claims, 5 Drawing Sheets

SURGICAL MICROSCOPE HAVING AN ILLUMINATING ARRANGEMENT

CROSS REFERENCE TO RELATED APPLICATIONS

This application claims priority of U.S. provisional application Ser. No. 61/272,039, filed Aug. 11, 2009, and also claims priority of German patent application no. 10 2009 036 913.9, filed Aug. 11, 2009, and the entire contents of both of the above applications are incorporated herein by reference.

FIELD OF THE INVENTION

The invention relates to a surgical microscope having a microscope main objective for the visualization of an object plane in an object region. The microscope main objective is passed through by a first stereoscopic component beam path and a second stereoscopic component beam path. The surgical microscope further includes an adjustable illuminating arrangement having an illuminating optic with a beam deflection unit mounted on the side of the microscope main objective facing away from the object region in order to direct the illuminating light through the microscope main objective to the object region. In a first position of the illuminating arrangement, the illuminating light passes through the cross sectional area of the microscope main objective in an area section which at least partially surrounds the optical axis of the first stereoscopic component beam path and/or the optical axis of the second stereoscopic component beam path.

BACKGROUND OF THE INVENTION

A surgical microscope of the kind described above is known from US 2008/0297892. This surgical microscope is designed as an ophthalmologic surgical microscope. This surgical microscope has an illuminating arrangement with which an illuminating beam path can be adjusted with the illuminating beam path running coaxially to the stereoscopic viewing beam paths. The illuminating beam path is guided through the microscope main objective to the object region. For this purpose, a beam deflection unit is provided for the surgical microscope which is configured as a beam splitter. With the beam deflection unit, the illuminating light is superposed on the left and right stereoscopic beam paths. This illuminating beam path makes possible the examination of the patient eye with excellent contrast with red reflection illumination.

Ophthalmologic surgical microscopes having an illuminating arrangement for red reflection illumination are used in cataract surgery.

In ophthalmology, so-called slit lamps are applied in order to visualize membranes in the vitreous body of a patient eye or to make structures on the retina and on the cornea of the patient eye visible. With this apparatus, a very bright slit-shaped, sharply limited light beam can be thrown from the side onto the patient eye in order to examine the same with this illumination using the microscope. This illuminating configuration is especially used in retina surgery.

Accordingly, for ophthalmologic surgical microscopes, there is the need that this is equipped for red reflection illumination as well as for slit illumination.

In retina surgery, surgical microscopes are used wherein a slit illumination module is mounted on the side facing toward the object region and ahead of the microscope main objective.

In this way, a patient eye can be examined with slit illuminating light which incidents on the object region at a large inclined angle of incidence. However, such a silt illuminating module reduces the free work space under the surgical microscope. In addition to the light source for the illuminating arrangement of the surgical microscope, an additional light source is needed for one such slit illumination module. Accordingly, a sterile manipulation of corresponding slit illuminating modules is difficult in day to day surgery.

There are surgical microscope known having an illuminating arrangement for the slit illumination wherein the slit illuminating light is guided through the microscope main objective to the object region. Corresponding surgical microscopes are described, for example, in EP 1 300 109 A1 or in US 2006/0238711 A1. In the surgical microscopes known from US 2006/0238711 A1 or EP 1 300 109 A1, the adjustment of a beam path for red reflection illumination is, however, not provided.

SUMMARY OF THE INVENTION

It is an object of the invention to provide a surgical microscope which is suitable to the same extent for use in cataract surgery as well as for retina surgery.

The object is achieved with a surgical microscope of the kind described above wherein, in at least one further position of the illuminating arrangement, the illuminating light passes through the cross sectional surface of the microscope main objective in an area section whose area centroid is spaced from the optical axis of one stereoscopic component beam path by more than the stereo basis of the two stereoscopic component beam paths from the optical axis of the other stereoscopic component beam path.

The invention is based on the realization that the viewing image of a patient eye, which is perceived by a viewing person in a surgical microscope, has excellent contrast with a slit illumination when the angle of incidence for the illuminating light is as large as possible with reference to the optical axis of at least one stereoscopic viewing beam path. The surgical microscope of the invention has the functionality of a classical slit lamp microscope and nonetheless provides a large free work space for the microscope main objective.

Preferably, the beam deflection unit is a mirror which has a part mirrored reflecting surface which is passed through by the first stereoscopic component beam path and/or by the second stereoscopic component beam path. In this way, in the surgical microscope, an illuminating beam path optimized for red reflection illumination can be adjusted which runs coaxially to the viewing beam paths.

On the mirror, it is also advantageous to provide a full mirrored surface in order to direct illuminating light to the object region. In this way, the illuminating light can be directed onto the object region without mirror losses. The mirror is preferably mirror symmetrical to an axis which perpendicularly intercepts the stereo basis of the stereoscopic component beam paths at the center. With this measure, it is ensured that the imaging and illuminating relationships in the two stereoscopic component beam paths correspond to each other.

In the first position of the illuminating arrangement, the illuminating optic images a light exit plane for the illuminating light at infinity or virtually to infinity or images an aperture diaphragm at infinity or virtually to infinity with the aperture diaphragm being arranged in a plane conjugated to this plane. In the examination of the patient eye with the surgical microscope, there then arises an image of the aperture diaphragm on the retina because of the refractive power of the cornea and lens. In this way, a patient eye can be visualized with excellent red reflection contrast using the surgical microscope.

In a further position of the illuminating arrangement, the field diaphragm is imaged in a field diaphragm plane in the object region arranged close to the object plane. In that this field diaphragm is configured as a slit diaphragm, the ophthalmologic surgical microscope is capable of examining the patient eye with slit illuminating light which is incident on the object region at a large angle inclined to the optical axis of a viewing beam path. Preferably, an adjustment of the size of the slit diaphragm is provided. This functionality can, for example, be realized with slit diaphragms of different sizes which can be moved in the corresponding illuminating beam path. The possibility of a continuous adjustment of width and height of corresponding slit diaphragms is, however, also advantageous. It is especially advantageous to provide a rotatability of the slit diaphragms in the illuminating beam path. This enables a viewing person to select different slit illumination configurations.

For a surgical microscope, it is advantageous when at least two different positions of the illuminating arrangement are provided wherein the illuminating light passes through the cross sectional surface of the microscope main objective in an area section whose area centroid is spaced from the optical axis of one stereoscopic component beam path by more than the stereo basis of the two stereoscopic component beam paths from the optical axis of the other stereoscopic component beam path. In this way, a viewing person can adapt the slit illumination to the inclination of the surface of an investigated object field. Especially, a viewing person is then capable to so influence illuminating reflections on the cornea so that the illuminating reflections disturb the viewing image only very little.

In a further embodiment of the invention, a movable light exit section is provided in the ophthalmologic surgical microscope which makes available illuminating light in a first position which passes through the cross sectional surface of the microscope main objective in an area section which at least partially surrounds the optical axis of the first stereoscopic component beam path and/or the optical axis of the second stereoscopic component beam path. Here, it is preferable to configure the light exit section to be movable about a pivot axis. By pivoting the light exit section, the angle of incidence for the illuminating light can be adjusted with reference to the optical axis of the microscope main objective and the stereoscopic component beam paths for viewing the object. This measure ensures that, while using only a single light source by means of the illuminating arrangement, the illuminating configurations desired in ophthalmologic surgical microscopes can be adjusted for slit illumination, surround field illumination as well as red reflection illumination. Principally, it is also possible to provide a lateral displacement movement in place of a pivot movement for the light exit section.

Preferably, the light exit section is the end of a light conductor. The light exit section can, however, also be configured as a light source such as a light emitting diode (LED), a xenon lamp or a halogen lamp.

It is especially advantageous to provide several pivot positions for the light exit section whereat the illuminating light is made available which passes through the cross sectional surface of the microscope main objective in an area section whose area centroid is spaced from the optical axis of one stereoscopic component beam path by more than the stereo basis of the two stereoscopic component beam paths from the optical axis of the other stereoscopic component beam path.

With this measure, it is ensured that the illuminating light is directed to the object region inclined to the optical axis of the two stereoscopic component beam paths. Then, membranes in vitreous bodies and structures on the cornea of the patient eye can be visualized with good contrast.

In a further embodiment of the invention, a light exit section for making available illuminating light is provided in a first position of the illuminating arrangement which passes through the cross sectional surface of the microscope main objective in an area section which at least partially surrounds the optical axis of the first stereoscopic component beam path and/or the optical axis of the second stereoscopic component beam path. In this way, a patient eye can be visualized with a contrast rich red reflection image.

In a further embodiment of the invention, a further beam deflecting unit for illuminating light is provided on the side of the microscope main objective which faces away from the object region in order to direct illuminating light to the object region for a surround field illumination. In this way, in the surgical microscope, two or more beam paths for illuminating light can be guided simultaneously to the object region.

It is advantageous when the light conductor in the illuminating arrangement has a second light exit section from which the illuminating light can be guided to a further beam deflecting unit in the first position of the illuminating arrangement. This illuminating light passes through the cross sectional surface of the microscope main objective in an area section whose area centroid is spaced from the optical axis of the stereoscopic component beam paths.

A compact configuration of the illuminating arrangement is made possible in that, in a further position of the illuminating arrangement, the illuminating light, which exits from the second light exit section of the light conductor, is guided in a folded beam path to the beam deflection unit.

Preferably, the light exit section is the end of the light conductor which is accommodated in a pivot lever pivotable about a pivot axis. The light conductor can be connected to the pivot lever without a complex rotational coupling in that the pivot lever has a flange section, which accommodates the light conductor, on which the light conductor is guided into the pivot lever with the light conductor being aligned with the pivot axis of the pivot lever.

Preferably, a condenser optic is provided which is movement coupled to the light conductor. In the first position and in the second further position of the illuminating arrangement, the condenser optic directs the illuminating light which exits from the second light exit section of the light conductor to the object region.

These measures minimize the structural space for the illuminating arrangement in the surgical microscope.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
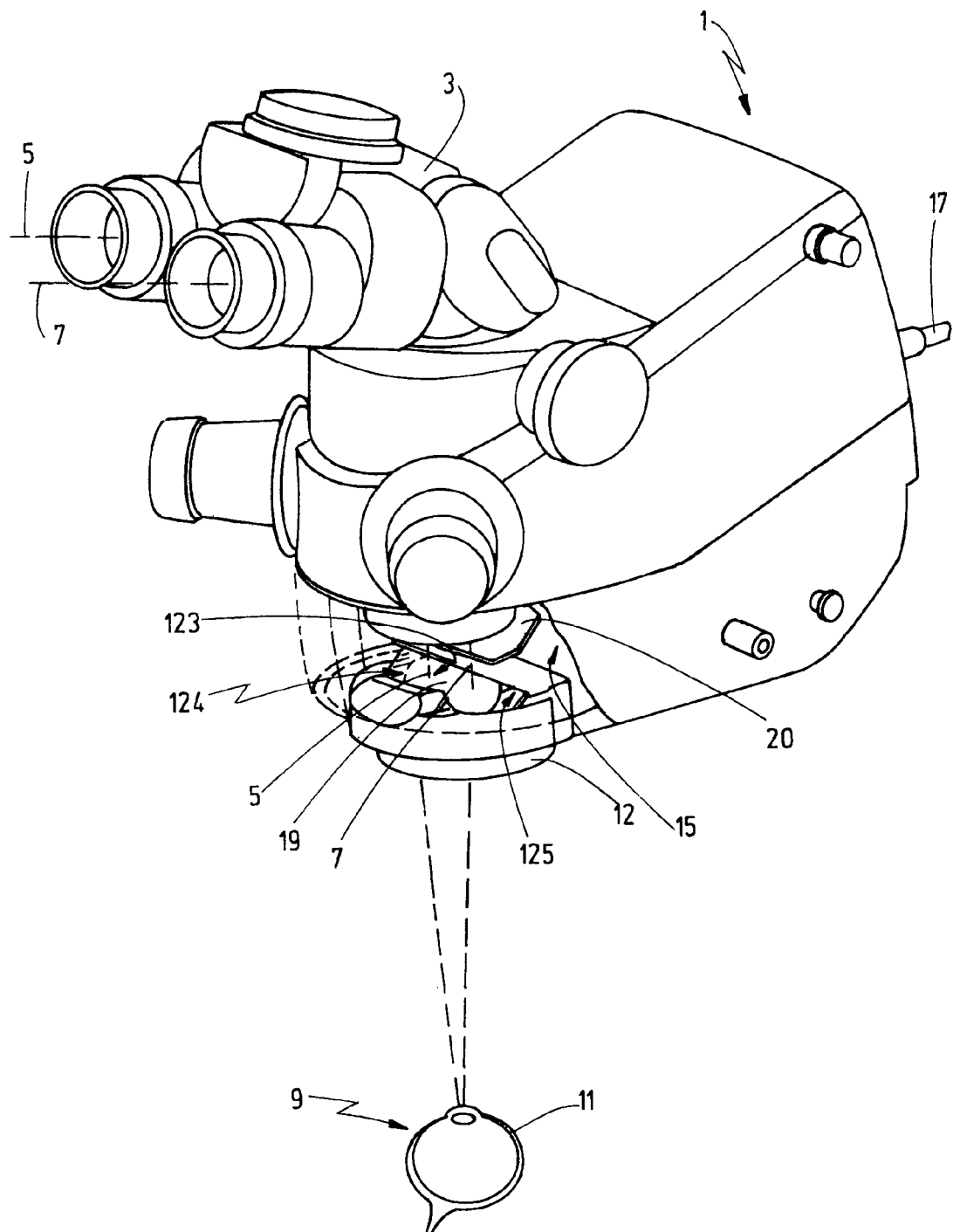
FIG. 1 is a surgical microscope having an illuminating arrangement with the surgical microscope being configured as an ophthalmologic surgical microscope.

The ophthalmologic surgical microscope 1 is shown in FIG. 1 and has a binocular tube 3 and a microscope main objective 12. A viewing person can view a patient eye 11 in an object region 9 under magnification through the binocular tube 3 with stereoscopic component beam paths (5, 7).

The ophthalmologic surgical microscope 1 is accommodated on a stand (not shown). The ophthalmologic surgical microscope 1 has an illuminating arrangement 15. The illuminating arrangement 15 is supplied with light via a light conductor 17 from a light source mounted on the stand of the ophthalmologic surgical microscope. The illuminating arrangement 15 includes an illuminating optic having an illuminating mirror 19 and an illuminating mirror 20. The illuminating light is directed through the microscope main objective 12 to the object region 9 via the illuminating mirrors (19, 20).

The illuminating mirror 19 has a partially mirrored region 123 and first and second fully mirrored regions (124, 125). In the partially mirrored region 123, the stereoscopic component beam paths (5, 7) pass through the illuminating mirror.

Figures 2, 3:
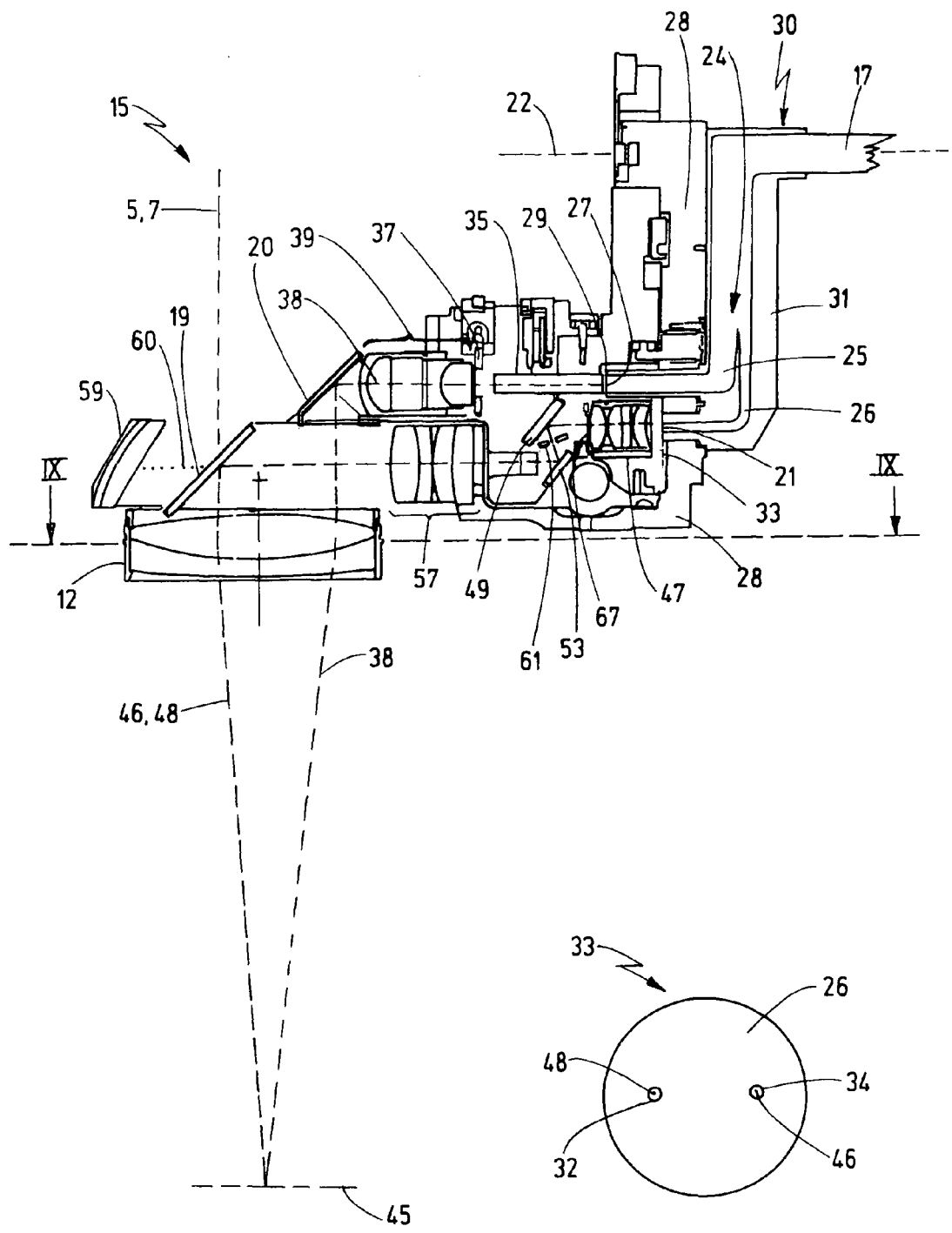
FIG. 2 is a section view of the illuminating arrangement in the ophthalmologic surgical microscope having the microscope main objective.
FIG. 3 is the light exit section of the light conductor of the illuminating arrangement.

FIG. 2 shows the illuminating arrangement 15 in the ophthalmologic surgical microscope 1 and the microscope main objective 12 is shown in section. The illuminating arrangement 15 includes a pivot lever 28 rotatably journalled in a pivot axis 22. The pivot position of the pivot lever 28 shown in FIG. 2 corresponds to a first position of the illuminating arrangement 15. The pivot lever 28 can be pivoted out of this pivot position into a first further pivot position and into a second pivot position. The first further pivot position of the pivot lever 28 and the second further pivot position of the pivot lever 28 correspond to a first further position and a second further position of the illuminating arrangement 15.

FIG. 2 shows the pivot lever 28 in the start position. The pivot lever 28 functions to accommodate a light conductor 17. The light conductor 17 is introduced into a light conductor housing 31 on a holding section 30 accommodating the light conductor. The light conductor housing 31 is connected to the pivot lever 28. The section 30 aligns with the pivot axis 22 of the pivot lever 28. In the light conductor housing 31, a branching 24 of the light conductor 17 is provided. A light conductor path 25 of the light conductor 17 is led to a first light exit section 27. The light exit section 27 is disposed in a light exit plane 29. A further light conductor path 26 of the light conductor 17 makes illuminating light available at a second light exit section 21 which is disposed in a light exit plane 33.

FIG. 3 shows the light exit plane 33 on the light exit section 21 of light conductor 17. The light conductor path 26 has a point-shaped light exit opening 32 and a point-shaped light exit opening 34.

In the position of the pivot lever 28 of FIG. 2, the illuminating light, which exits from the light exit section 27, passes through a glass rod 35 in order to illuminate a field diaphragm 37. The glass rod 35 acts as a homogenizer. The illuminating beam path 38 is then guided through a collector optic system 39. The illuminating beam path 38 is guided to the object region through the microscope main objective 12 by means of the beam deflecting element configured as mirror 20. The collector optic system 39 and the microscope main objective 12 image the field diaphragm 37 into the object plane 45.

The illuminating light, which exits from the second light exit section 21 of the light conductor 17, passes, in the first position of the pivot lever 28, through the collector optic system 47 with an illuminating beam path (46, 48). At the output end of the collector optic system 47, the illuminating light passes through a field diaphragm 67. The illuminating light, which passes through the illuminating field diaphragm 67, is guided via a folded beam path via deflecting mirrors (49, 53) to a condenser optic system 57. From there, the illuminating light arrives at an illuminating mirror 19. The condenser optic system 57 is accommodated in the pivot lever 28. The illuminating beam path (46, 48) is superposed onto the stereoscopic component beam paths (5, 7) by means of the illuminating mirror 19. The illuminating mirror 19 is provided with a part mirrorization in the region 123 passed through by the stereoscopic component beam paths (5, 7). Because of the part mirrorization, the illuminating mirror 19 deflects a 30% portion of the illuminating light with the illuminating beam path (46, 48) coaxially to the optical axes of the stereoscopic component beam paths (5, 7) through the microscope main objective 12 to the object region 9.

The part mirroring of the illuminating mirror 19 is so configured that a 70% portion of the illuminating light, which incidents thereon, is not deflected. In this way, it is ensured that here 30% of the illuminating light is directed to the object region. A light trap 59 is provided in the illuminating arrangement 15 so that the illuminating light, which is not deflected by the illuminating mirror 19, causes no reflections in the stereoscopic component beam paths (5, 7) which would disturb the object viewing. In the light trap 59, the illuminating light 60 which passes through the illuminating mirror 19 is absorbed.

In the folded section of the illuminating path (46, 48), an aperture diaphragm 61 is mounted between the deflecting mirrors 49 and 53. The aperture diaphragm 61 is disposed in a plane conjugated to the light exit plane of the second light exit section 21 of the light conductor 17. The condenser optic system 57 effects an imaging of the field diaphragm 67 in the object plane 45 via the illuminating mirror 19 and the microscope main objective 12. The aperture diaphragm 61 is imaged at infinity or almost at infinity. The imaging beam paths for the aperture diaphragm 61 therefore incident with more or less parallel rays onto the patient eye. During the examination of a patient eye, the aperture diaphragm 61 is more or less imaged sharply onto the ocular fundus because of the refractive power of the cornea and the natural lens. The imaging beam path for the aperture diaphragm 61 and the field diaphragm 67 is guided coaxially to the optical axis of the stereoscopic component beam paths (5, 7).

Figure 4:
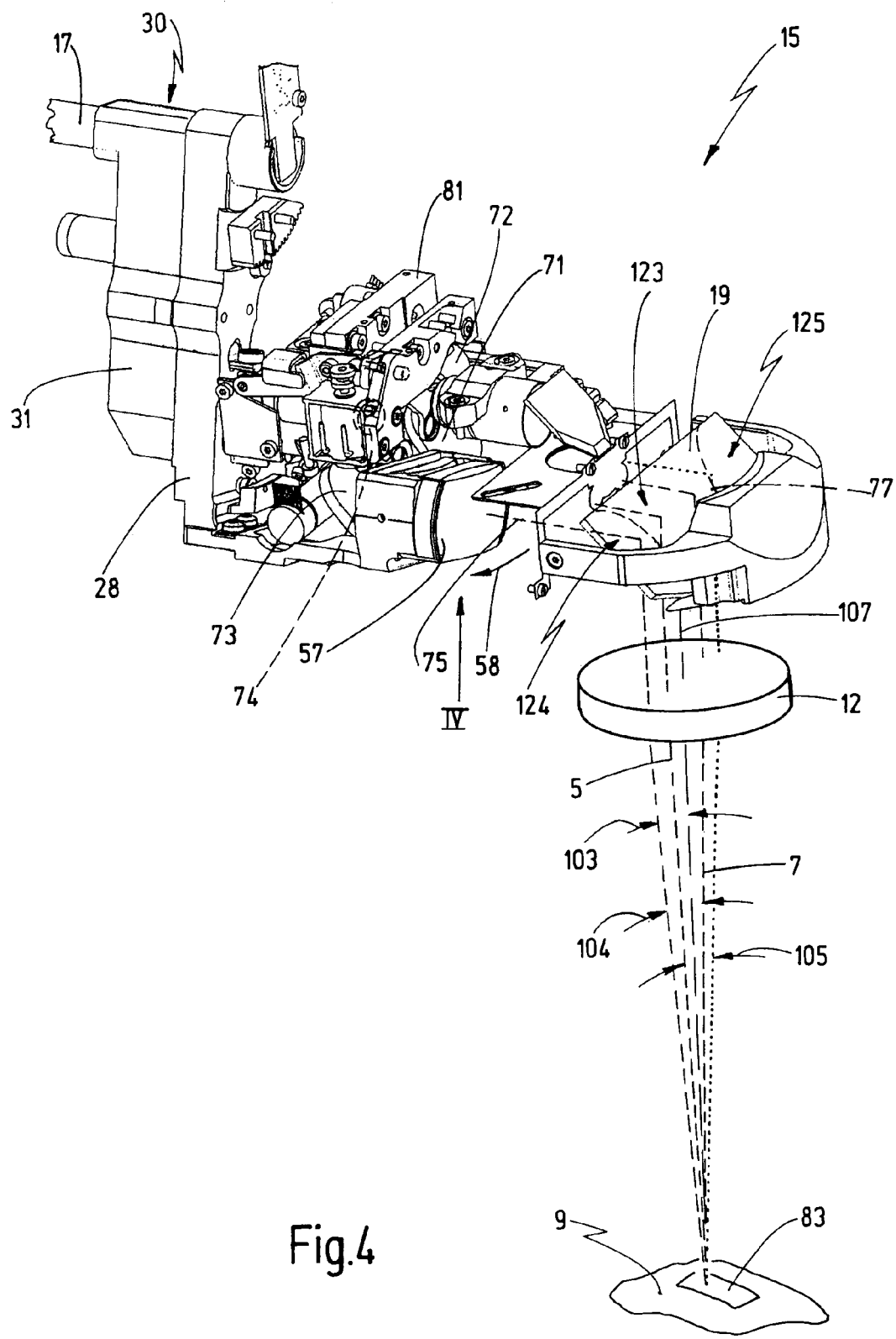
FIG. 4 is a perspective view of the illuminating arrangement.

FIG. 4 shows the illuminating arrangement 15 in the first further position with a pivot lever 28 shifted relative to FIG. 2. The pivot lever 28 is pivoted into the first further pivot position. The condenser optic system 57 is accommodated on the pivot lever 28 and is shifted relative to the position of the illuminating arrangement 15 shown in FIG. 2 in the direction of arrow 58. In this pivot position of the pivot lever 28, the light from the first light exit section 27 of the light conductor 17 passes through a slit diaphragm unit 81 having adjustable slit diaphragms. The light is then directed with a folded beam path via mirrors (73, 74) through the condenser optic system 57. Finally, the light impinges with the illuminating beam path 75 on the illuminating mirror 19 which guides the light through the microscope main objective 12 to the object region 9 in order to there generate a slit image 83.

Figure 5:
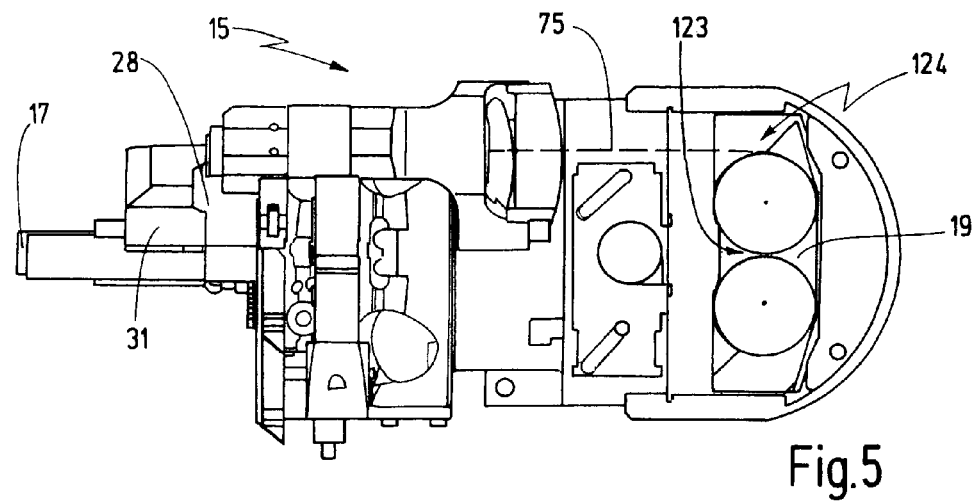

FIG. 5 shows the illuminating arrangement 15 in this position with the viewing direction of arrow IV of FIG. 4. Here, the pivot lever 28 is set in the first further pivot position. The illuminating light is then guided with an illuminating beam path 75 through the condenser optic system 57 to the illuminating mirror 19. The condenser optic system 57 is coupled to the pivot lever 28. The illuminating light, which incidents on the illuminating mirror 19, is here guided, in part, by reflection in the part mirrored region 123 and by reflection in the full mirrored region 124 through the microscope main objective 12 to the object region 9.

Figure 6:
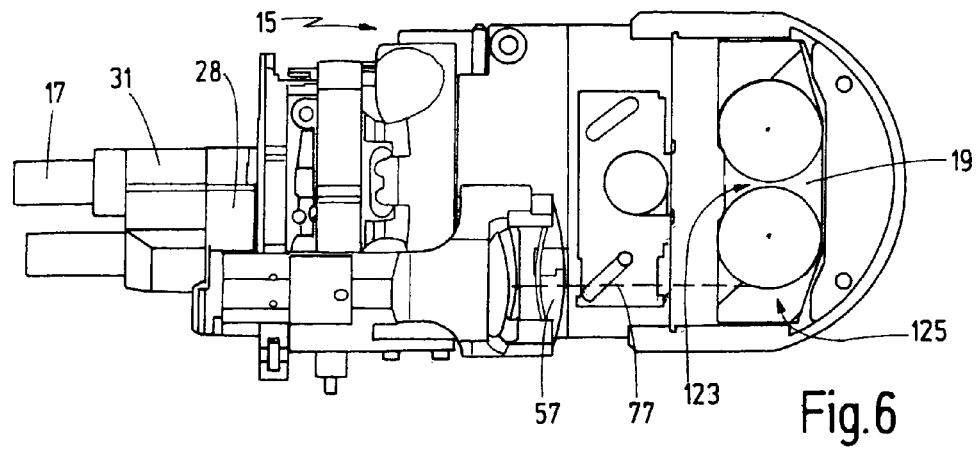
FIGS. 5, 6 and 7 show different positions of the illuminating arrangement.

FIG. 6 shows a corresponding view of the illuminating arrangement 15 wherein the pivot lever 28 is disposed in a second pivot position different from the first pivot position. Here too, the illuminating light is guided through the slit diaphragm unit 81 having adjustable slit diaphragms. The illuminating light is directed with a folded beam path via the mirrors (71, 72), which are shown in FIG. 4, through the condenser optic system 57. From there, the illuminating beam path 77 arrives at the illuminating mirror 19. The mirror 19 directs the light because of the reflections in the part mirrored region 123 and in the full mirrored region 125 again through the microscope main objective 12 to the object region 9. Also in this position, a slit image arises in the object region 9.

Figure 7:
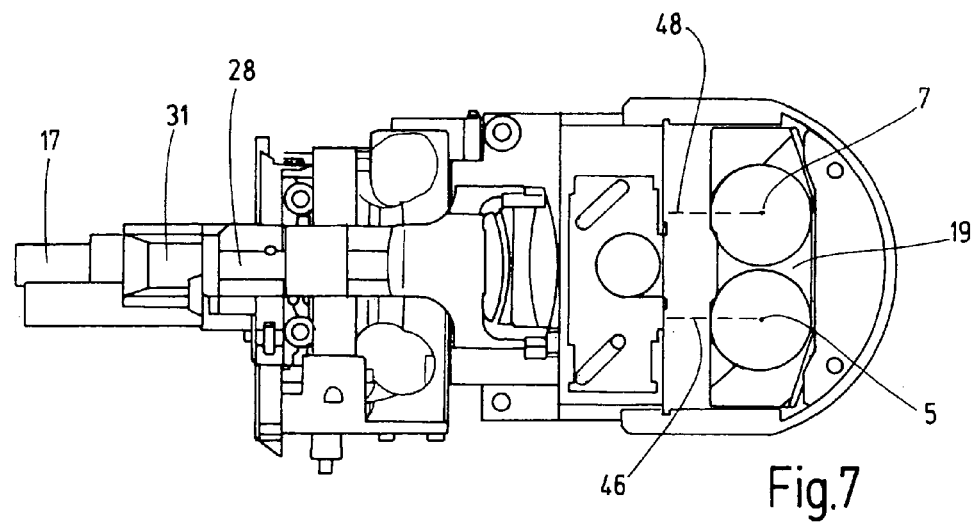

FIG. 7 shows the illuminating arrangement 15 in the first position. Here, the illuminating mirror 19 directs the illuminating beam path (46, 48) coaxially to the optical axes of the stereoscopic component beam paths (5, 7) through the microscope main objective 12 to the object region 9. In this position of the illuminating arrangement 15, the illuminating light, which exits from the light exit section 27 of the light conductor 17, is guided by the mirror 20 shown in FIG. 2 to the object region 9.

Accordingly, with light from the light exit section 27, light for a surround field illumination as well as for a slit illumination can be provided.

Figure 8:
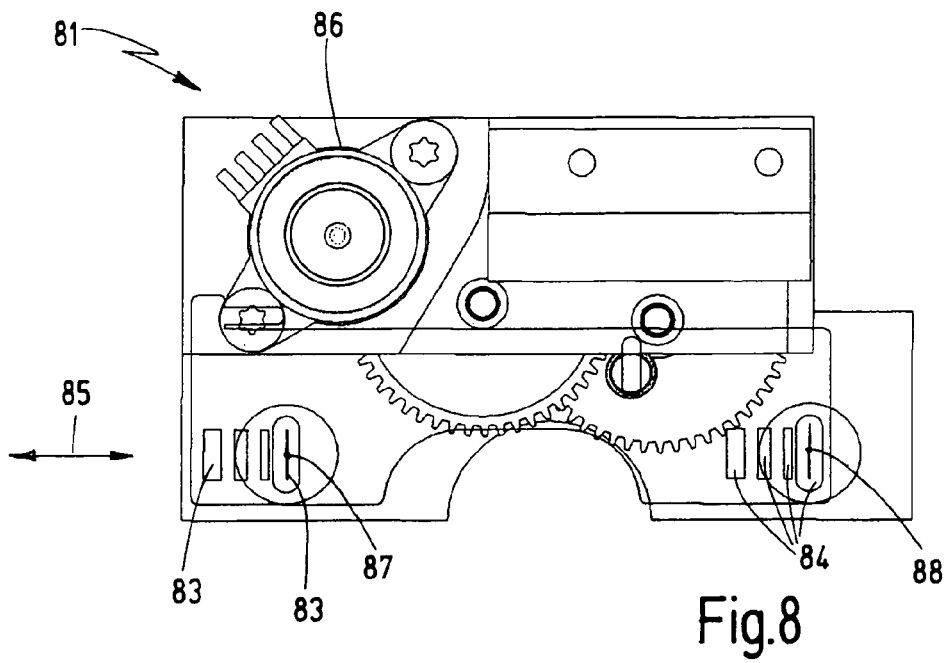
FIG. 8 shows a slit diaphragm system of the illuminating arrangement.

The slit diaphragm system 81 of the illuminating arrangement 15 is shown in FIG. 8. The slit diaphragm system 81 comprises slit diaphragms (83, 84) of different size which are displaceable corresponding to the arrow 85. The slit diaphragm system 81 includes an electrical drive 86 by means of which the slit diaphragms (83, 84) can be moved into the optical axis (87, 88) of the illuminating beam path (75, 77). With the electric drive 86, positions of the slit diaphragm outside of the optical axis (87, 88) can also be adjusted. This makes possible a variation of the slit illumination angle with reference to the optical axis 107 of the microscope main objective 12. With the ophthalmologic surgical microscope 1 shown in FIG. 1, a viewing person can thereby visualize a patient eye in the object region with slit images which are of different size. Optionally, a rotatability of the slit diaphragms (83, 84), which are mounted in the illuminating beam path (75, 77), can also be provided. This makes it possible for an illumination plane to adapt the orientation of the slit images to an object structure in the object region. Furthermore, it is advantageous to also provide a continuous variability of the width and height of the slit diaphragms (83, 84) in the illuminating beam path (75, 77).

Figure 9:
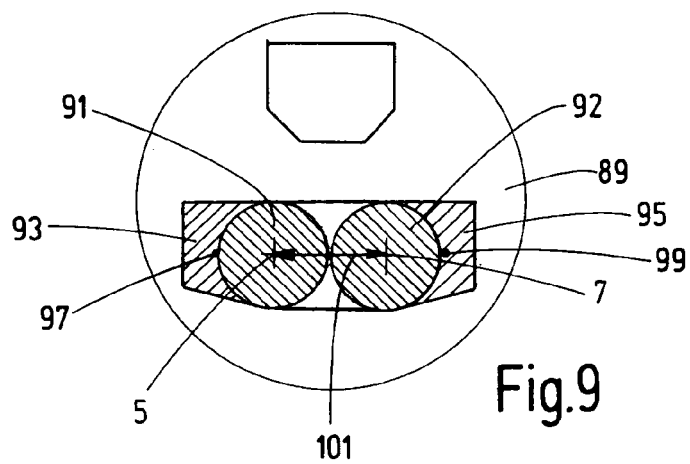
FIG. 9 is a section of the microscope main objective in the surgical microscope taken along line IX-IX of FIG. 2; and, FIG. 10 shows an illuminating mirror in the surgical microscope.

FIG. 9 shows a section of the microscope main objective 12 in the ophthalmologic surgical microscope 1 along line IX-IX of FIG. 2. In the first position of the illuminating arrangement 15, the illuminating light passes through the cross sectional surface 89 of the microscope main objective 12 and is superposed onto the stereoscopic component beam paths (5, 7) with a beam path which runs coaxially to the optical axis of the stereoscopic component beam paths (5, 7). In this way, the surface section (91, 92), wherein the illuminating light passes through cross sectional surface 89 of the microscope main objective, surrounds the optical axes of the two component beam paths (5, 7).

However, if the pivot lever 28 of the illuminating arrangement 15 is moved into the first or second pivot position, then the illuminating light of the illuminating beam path passes through the cross sectional surface 89 of the microscope main objective 12 having an area section 93 and an area section 95 having respective centroids 97 and 99 spaced from the optical axis of one of the two component beam paths 5 or 7 by more than the stereo basis 101 of the two stereoscopic component beam paths (5, 7) from the optical axis of the other stereoscopic component beam path 7 or 5.

As shown in FIG. 4, the illuminating light, which exits from the light exit section 27 of the light conductor 17 for a pivot position of the pivot lever 28, is guided with an illuminating beam path (75, 77) to the object region 9 whose optical axis defines an angle 103 of approximately 6° with the optical axis 107 of the microscope main objective 12. In this way, it is achieved that in a pivot position of the pivot lever 28 of the illuminating arrangement 15, the illuminating light, which exits from the light exit section 27 of light conductor 17, is guided with an illuminating beam path 75 to the object region 9 which has an optical axis which is at an angle 104 to the optical axis of the viewing beam path 7 which is clearly more than 10°.

In another pivot position of the pivot lever 28, the illuminating light from the light conductor 17 arrives at the object region 9 with an illuminating beam path 77 having an optical axis which defines an angle 105 with the optical axis of the component beam path 5 which is greater than 10°.

Figure 10:
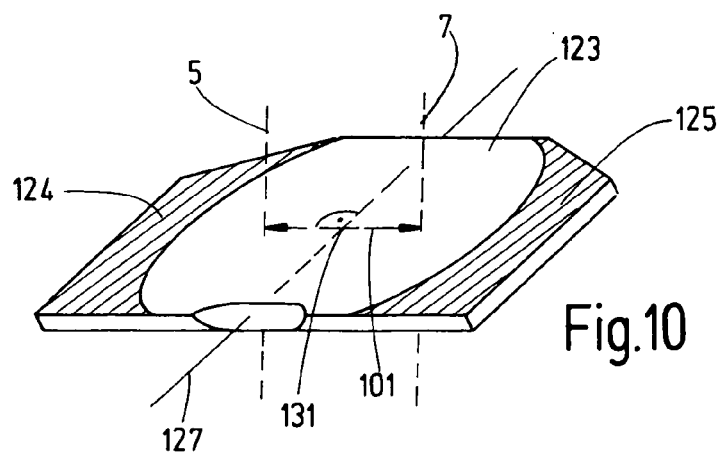

FIG. 10 shows the illuminating mirror 19 in the ophthalmologic surgical microscope 1. The illuminating mirror 19 has a region 123 having a part mirrored mirror surface which is passed through by the microscope component beam paths (5, 7). In the regions 124 and 125, the illuminating mirror is provided with a full mirrored mirror surface. The full mirrored mirror surfaces in the regions 124 or 125 direct the illuminating light to the object region 9 without mirror losses in the pivot positions of the pivot lever 28. The geometry of the illuminating mirror 19 is symmetrical to axis 127 which intercepts the stereo basis 101 of the stereoscopic component beam paths (5, 7) perpendicularly at the center 131.

In summary, it is noted that the invention is directed to a surgical microscope 1 having a microscope main objective 12 for the visualization of an object plane 45 in an object region 9. The microscope main objective 12 is passed through by a first stereoscopic component beam path 5 and by a second stereoscopic component beam path 7. The ophthalmologic surgical microscope 1 includes an adjustable illuminating arrangement 15 which makes available illuminating light. The illuminating arrangement 15 has an illuminating optic having a beam deflection unit 19 which is mounted on the side of the microscope main objective 12 facing away from the object region 9 in order to direct the illuminating light through the microscope main objective 12 to the object region 9. In a first position of the illuminating arrangement 15, the illuminating light passes through the cross sectional area 89 of the microscope main objective 12 in an area section (91, 92) which at least partially surrounds the optical axis of the first stereoscopic component beam path 5 and/or the optical axis of the second stereoscopic component beam path 7. According to the invention, in at least one further position of the illuminating arrangement 15, the illuminating light passes through the cross sectional area 89 of the microscope main objective 12 in an area section (93, 95) whose area centroid (97, 99) is spaced from the optical axis of one of the two component beam paths (7, 5) by more than the stereo basis 101 of the two stereoscopic component beam paths (5, 7) from the optical axis of the other stereoscopic component beam path (7, 5).

It is understood that the foregoing description is that of the preferred embodiments of the invention and that various changes and modifications may be made thereto without departing from the spirit and scope of the invention as defined in the appended claims.

What is claimed is:

1. A surgical microscope defining first and second stereoscopic component beam paths and comprising:
a microscope main objective for visualizing an object plane in an object region;
said microscope main objective being mounted so as to cause said first and second stereoscopic component beam paths to pass there through;
said microscope main objective having a side facing away from said object region;
an adjustable illuminating arrangement for supplying an illuminating light;
said adjustable illuminating arrangement including an illuminating optic having a beam deflecting unit mounted on said side of said microscope main objective to direct said illuminating light through said microscope main objective to said object region;
said adjustable illuminating arrangement being movable into a first position wherein said illuminating light passes through the cross-sectional surface of said microscope main objective in an area section at least partially surrounding the optical axis of said first stereoscopic component beam path and/or the optical axis of said second stereoscopic component beam path;
said first and second stereoscopic component beam paths conjointly defining a stereo basis; and,
said adjustable illuminating arrangement being movable from said first position into a further position wherein said illuminating light passes through said cross-sectional surface in an area section having a centroid disposed at a distance from the optical axis of at least one of said stereoscopic component beam paths which is greater than said stereo basis of said first and second stereoscopic component beam paths.

2. The surgical microscope of claim 1, wherein, in said further position of said illuminating arrangement, said illuminating light passes through said cross-sectional surface of said microscope main objective in an area section having a centroid disposed at a distance from the optical axis of said first stereoscopic component beam path which is different from the distance of said centroid to the optical axis of said second stereoscopic component beam path.

3. The surgical microscope of claim 1, wherein said beam deflecting unit is a mirror having a region with a partly mirrored mirror surface through which said first stereoscopic component beam path and/or said second stereoscopic component beam path passes.

4. The surgical microscope of claim 3, wherein said mirror has a region having a fully mirrored mirror surface for directing said illuminating light to said object region.

5. The surgical microscope of claim 3, wherein said mirror is mirror symmetrical to an axis which perpendicularly intercepts said stereo basis at the center thereof.

6. The surgical microscope of claim 1, wherein said illuminating optic, in said first position of said illuminating arrangement, images a light exit plane for said illuminating light at infinity or almost at infinity or images an aperture diaphragm at infinity or almost at infinity, said aperture diaphragm being disposed in a plane conjugated to said light exit plane.

7. The surgical microscope of claim 1, wherein said illuminating optic, in said further position of said illuminating arrangement, images a field diaphragm into said object region.

8. The surgical microscope of claim 7, wherein said field diaphragm is a slit diaphragm.

9. The surgical microscope of claim 8, wherein said slit diaphragm has a width and/or height which is adjustable.

10. The surgical microscope of claim 9, wherein said slit diaphragm has a width and/or height which is continuously adjustable.

11. The surgical microscope of claim 9, wherein said slit diaphragm is rotatable in the illuminating light path.

12. The surgical microscope of claim 1, wherein said further position is a first further position; said illuminating arrangement is movable into a second further position different from said first further position; and, said illuminating light, in said first further position, passes through said cross-sectional surface of said microscope main objective in an area section having a centroid disposed at a distance from the optical axis of one of the stereoscopic component beam paths which is greater than or less than the distance of said centroid of said cross-sectional surface of said microscope main objective from the optical axis of said one of the stereoscopic component beam paths.

13. The surgical microscope of claim 1, wherein said illuminating arrangement includes a movable light exit section having a first position wherein said light exit section makes illuminating light available which passes through the cross-sectional surface of said microscope main objective in an area section which at least partially surrounds the optical axis of said first stereoscopic component beam path and/or the optical axis of said second stereoscopic component beam path.

14. The surgical microscope of claim 13, wherein said light exit section is movable about a pivot axis.

15. The surgical microscope of claim 14, wherein said light exit section has a first light exit area and a second light exit area formed therein.

16. The surgical microscope of claim 13, wherein said illuminating arrangement comprises a light conductor having an end defined by said light exit section.

17. The surgical microscope of claim 16, wherein said adjustable illuminating arrangement further comprises a pivot lever pivotable about a pivot axis; a light conductor housing for accommodating said light conductor therein; and, said light conductor housing is mounted on said pivot lever.

18. The surgical microscope of claim 17, wherein said pivot lever has a section accommodating said light conductor; said light conductor is introduced into said light conductor housing on said section of said pivot lever; and, said light conductor housing is aligned with said pivot axis.

19. The surgical microscope of claim 1, wherein said adjustable illuminating arrangement comprises a movable light exit section which, in at least one position, makes illuminating light available which passes through said cross-sectional surface of said microscope main objective in an area section having a centroid spaced from the optical axis of one of said stereoscopic component beam paths by more than said stereo basis from the optical axis of the other one of said stereoscopic component beam paths.

20. The surgical microscope of claim 19, wherein said movable light exit section is movable between a first position and a second position different from said first position; and, in said second position, the illuminating light made available passes through the cross-sectional surface of said microscope main objective in an area section having a centroid spaced from the optical axis of one of said first and second stereoscopic component beam paths by more than said stereo basis from the optical axis of the other one of said stereoscopic component beam paths.

21. The surgical microscope of claim 20, wherein said illuminating arrangement includes a light conductor; and, said light exit section is the end of said light conductor.

22. The surgical microscope of claim 21, wherein said illuminating arrangement further comprises a pivot lever pivotable about a pivot axis; and said light conductor is accommodated in said pivot lever.

23. The surgical microscope of claim 22, wherein said illuminating arrangement comprises a light conductor housing having a flange section accommodating said light conductor; said light conductor is guided into said light conductor housing on said flange section; and, said light conductor is aligned with said pivot axis of said pivot lever.

24. The surgical microscope of claim 23, said illuminating arrangement including a condenser optic movably coupled to said light conductor; and, said condenser optic directing the illuminating light exiting from said light exit section of said light conductor in the first position and in the second further position of said illuminating arrangement to said object region.

25. The surgical microscope of claim 24, wherein, in said further position of said illuminating arrangement, the illuminating light, which exits from said light exit section of said light conductor, is guided via a folded beam path to said beam deflecting unit.

26. The surgical microscope of claim 23, wherein said beam deflecting unit is a first beam deflecting unit; said illuminating arrangement further comprises a second beam deflection unit for illuminating light to direct illuminating light to said object region for surround-field illumination; and, said second beam deflection unit is accommodated on said side of said microscope main objective facing away from the object region.

* * * * *